US010925568B2

(12) United States Patent
Lu et al.

(10) Patent No.: US 10,925,568 B2
(45) Date of Patent: Feb. 23, 2021

(54) APPARATUS AND METHOD USING PHYSICAL MODEL BASED DEEP LEARNING (DL) TO IMPROVE IMAGE QUALITY IN IMAGES THAT ARE RECONSTRUCTED USING COMPUTED TOMOGRAPHY (CT)

(71) Applicant: CANON MEDICAL SYSTEMS CORPORATION, Otawara (JP)

(72) Inventors: Yujie Lu, Vernon Hills, IL (US); Zhou Yu, Vernon Hills, IL (US); Jian Zhou, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 1 day.

(21) Appl. No.: 16/510,632

(22) Filed: Jul. 12, 2019

(65) Prior Publication Data
US 2021/0007695 A1 Jan. 14, 2021

(51) Int. Cl.
*G06K 9/00* (2006.01)
*A61B 6/00* (2006.01)
(Continued)

(52) U.S. Cl.
CPC ............ *A61B 6/5205* (2013.01); *A61B 6/032* (2013.01); *A61B 6/4435* (2013.01); *G06N 3/08* (2013.01);
(Continued)

(58) Field of Classification Search
CPC combination set(s) only.
See application file for complete search history.

(56) References Cited

U.S. PATENT DOCUMENTS

| 2006/0210131 A1* | 9/2006 | Wheeler, Jr. | .......... G06T 11/008 |
| | | | 382/128 |
| 2013/0051519 A1* | 2/2013 | Yang | ..................... G06T 11/005 |
| | | | 378/19 |

(Continued)

FOREIGN PATENT DOCUMENTS

WO   WO 2017/223560 A1   12/2017

OTHER PUBLICATIONS

Wang, Z., et al., "Removing ring artifacts in CBCT images via generative adversarial networks with unidirectional relative total variation loss", Neural Computing and Applications, https://www.researchgate.net/publication/330346134_Removing_ring_artifacts_in_CBCT_images_via_generative adversarial_networks_with_unidirectional_relative_total_variation_loss, Jan. 2019.

(Continued)

*Primary Examiner* — Alex Kok S Liew
(74) *Attorney, Agent, or Firm* — Oblon, McClelland, Maier & Neustadt, L.L.P.

(57) ABSTRACT

A method and apparatus is provided that uses a deep learning (DL) network to improve the image quality of computed tomography (CT) images, which were reconstructed using an analytical reconstruction method. The DL network is trained to use physical-model information in addition to the analytical reconstructed images to generate the improved images. The physical-model information can be generated, e.g., by estimating a gradient of the objective function (or just the data-fidelity term) of a model-based iterative reconstruction (MBIR) method (e.g., by performing one or more iterations of the MBIR method). The MBIR method can incorporate physical models for X-ray scatter, detector resolution/noise/non-linearities, beam-hardening, attenuation, and/or the system geometry. The DL network can be trained using input data comprising images reconstructed using the (Continued)

analytical reconstruction method and target data comprising images reconstructed using the MBIR method.

20 Claims, 6 Drawing Sheets

(51) Int. Cl.
    *A61B 6/03*     (2006.01)
    *G06T 11/00*     (2006.01)
    *G06N 20/00*     (2019.01)
    *G06N 3/08*     (2006.01)

(52) U.S. Cl.
    CPC ............ *G06N 20/00* (2019.01); *G06T 11/003* (2013.01); *G06T 2207/10081* (2013.01); *G06T 2207/20081* (2013.01); *G06T 2207/20084* (2013.01); *G06T 2211/424* (2013.01)

(56) References Cited

U.S. PATENT DOCUMENTS

| | | | |
|---|---|---|---|
| 2016/0300369 A1 | 10/2016 | Silver et al. | |
| 2017/0294034 A1 | 10/2017 | Zhou et al. | |
| 2018/0018757 A1* | 1/2018 | Suzuki | A61B 6/03 |
| 2018/0197317 A1 | 7/2018 | Cheng et al. | |
| 2018/0349771 A1* | 12/2018 | Kamilov | G06T 11/003 |
| 2019/0035118 A1 | 1/2019 | Zhao et al. | |

OTHER PUBLICATIONS

T. Wurfl, et al, Deep learning computed tomography, 2016.
H.Chen, et al, Low-dose CT with a residual encoder-decoder convolutional neural network (RED-CNN), 2017.
E. Kang, et al, Wavelet domain residual network (WavResNet) for low-dose x-ray CT reconstruction. 2017.
Q. Yang, et al, CT image denoising with perceptive deep neural networks. 2017.
D. Wu, et al, Iterative low-dose CT reconstruction with priors trained by artificial neural network. 2017.
J. Wolterink, et al, Generative adversarial networks for noise reduction in low-dose CT. 2017.
Q. Yang, et al, Low dose CT image denoising using a generative adversarial network with wasserstein distance and perceptual loss. 2018.
W. Du, et al, Stacked competitive networks for noise reduction in low-dose CT. 2017.
K. Mentl, et al. Noise reduction in low-dose CT using a 3D multiscale sparse denoising autoencoder. 2017.
H. Shan, et al, 3D convolutional encoder-decoder network for low-dose CT via transfer learning from a 2D trained network. 2018.
L. Gjesteby, et al, Reducing metal streak artifacts in CT images via deep learning: Pilot results. 2017.
C. Zhang and Y. Xing, CT artifact reduction via U-net CNN. 2018.
H. Li and M. Klaus, Low-dose CT streak artifacts removal using deep residual neural network. 2017.
Adler, J. And Öktem, O. Solving ill-posed inverse problems using iterative deep neural networks. Inverse Problems, 2017.
Putzky P, and Welling M. Recurrent inference machines for solving inverse problems. arXiv. 2017.
Adler J, and Öktem O. Learned primal-dual reconstruction. IEEE transactions on medical imaging. 2018.
Gupta, Harshit, et al. CNN-Based Projected Gradient Descent for Consistent CT Image Reconstruction. IEEE transactions on medical imaging, 2018,.
Hein, Ilmar, et al. Three-Dimensional Two Material Based Beam Hardening Correction for Iterative Reconstruction. 2016.
De Man, Bruno, et al. Distance-driven projection and backprojection in three dimensions. https://www.ncbi.nlm.nih.gov/pubmed/15248590. 2004.

\* cited by examiner

APPARATUS AND METHOD USING PHYSICAL MODEL BASED DEEP LEARNING (DL) TO IMPROVE IMAGE QUALITY IN IMAGES THAT ARE RECONSTRUCTED USING COMPUTED TOMOGRAPHY (CT)

FIELD

This disclosure relates to using a physical model together with deep learning (DL) neural network to improve image quality in images that are reconstructed using computed tomography (CT).

BACKGROUND

The background description provided herein is for the purpose of generally presenting the context of the disclosure. Work of the presently named inventors, to the extent the work is described in this background section, as well as aspects of the description that cannot otherwise qualify as prior art at the time of filing, are neither expressly nor impliedly admitted as prior art against the present disclosure.

Medical imaging produces images of the internal members of a patient's body. Examples of tomographic medical-imaging modalities include X-ray computed tomography (CT). Once the images have been produced, a physician can use the images to diagnose a patient's injuries or diseases X-ray CT systems and methods are widely used, particularly for medical imaging and diagnosis. X-ray CT systems generally create images of one or more sectional slices through a subject's body. A radiation source, such as an X-ray source, irradiates the body from one side. At least one detector on the opposite side of the body receives radiation transmitted through the body. The attenuation of the radiation that has passed through the body is measured by processing electrical signals received from the detector.

A CT sinogram indicates attenuation through the body as a function of position along a detector array and as a function of the projection angle between the X-ray source and the detector array for various projection measurements. In a sinogram, the spatial dimensions refer to the position along the array of X-ray detectors. The time/angle dimension refers to the projection angle of X-rays, which changes as a function of time during a CT scan. The attenuation resulting from a point in the imaged object will trace out a sine wave around the vertical axis. Those points farther from the axis of rotation generate sine waves with larger amplitudes, and the phase of the sine waves corresponds to the angular positions of objects around the rotation axis. Performing an inverse Radon transform—or any other image reconstruction method—reconstructs an image from the projection data in the sinogram.

For example, filtered back-projection (FBP) is often used for analytical reconstruction of computed tomography (CT) images. Iterative reconstruction (IR) methods can achieve improved image quality relative to FBP methods, but this improvement comes at the expense of significant increases in time and computation. Accordingly, improved methods are desired that achieve improved image quality without the significant increase in time and computation that is typical of IR methods.

Analytical methods or IR methods can be used to reconstruct a volume image of the anatomy/structure within the patient. As discussed above, there is a trade-off between speed and image quality, with analytical methods providing faster image reconstruction and IR methods providing improved image quality. Thus improved methods are desired for achieving better image quality without sacrificing time and computation. That is, it would be desirable to have a method that combines (at least approximately) the computational speed of an analytical method with the image quality of an IR method.

BRIEF DESCRIPTION OF THE DRAWINGS

A more complete understanding of the disclosure is provided by reference to the following detailed description when considered in connection with the accompanying drawings, wherein.

DETAILED DESCRIPTION

Compared to analytical reconstruction methods for CT, iterative reconstruction (IR) methods can achieve improved image quality by exploring statistical properties of measurements. Model-based iterative reconstruction (MBIR) methods can generate even better image quality than IR methods through incorporating physical models of the CT system and scanned objects. However, MBIR methods are not more widely adopted because MBIR methods suffer from slow reconstruction speed, and accurate physical models require increased computations, slowing down iterative image reconstruction.

One approach to achieving an optimal compromise in the trade-off between computational complexity/speed and image quality is to first use an analytical reconstruction method to reconstruct an initial CT image, and then use a deep learning (DL) network (also referred to as an artificial neural network (ANN) or as a convolutional neural network (CNN)) to filter the initial CT image and generate a final CT image. The DL network can be trained using training data in which the input data are analytical reconstructed images and the target images are IR reconstructed images, such that, in response to an input of analytical reconstructed image, the DL network learns to output an image approximating the image quality of an IR reconstructed image. Because the DL network is fast compared an IR methods and MBIR methods, the combination of the analytical reconstruction method together with the DL network is both fast and can provide image quality comparable to MBIR methods (at least in theory). However, in practice, it can be challenging to achieve image quality comparable to the IR CT method when only the analytical reconstructed image is provided as an input. This changes when physical-model information/data is also used as an input to the DL network.

Accordingly, for the inputs into the DL network, the methods described herein use, in addition to the analytical reconstructed image, information from one or more physical models to improve the ability of the DL network to achieve high image quality.

Figure 1:
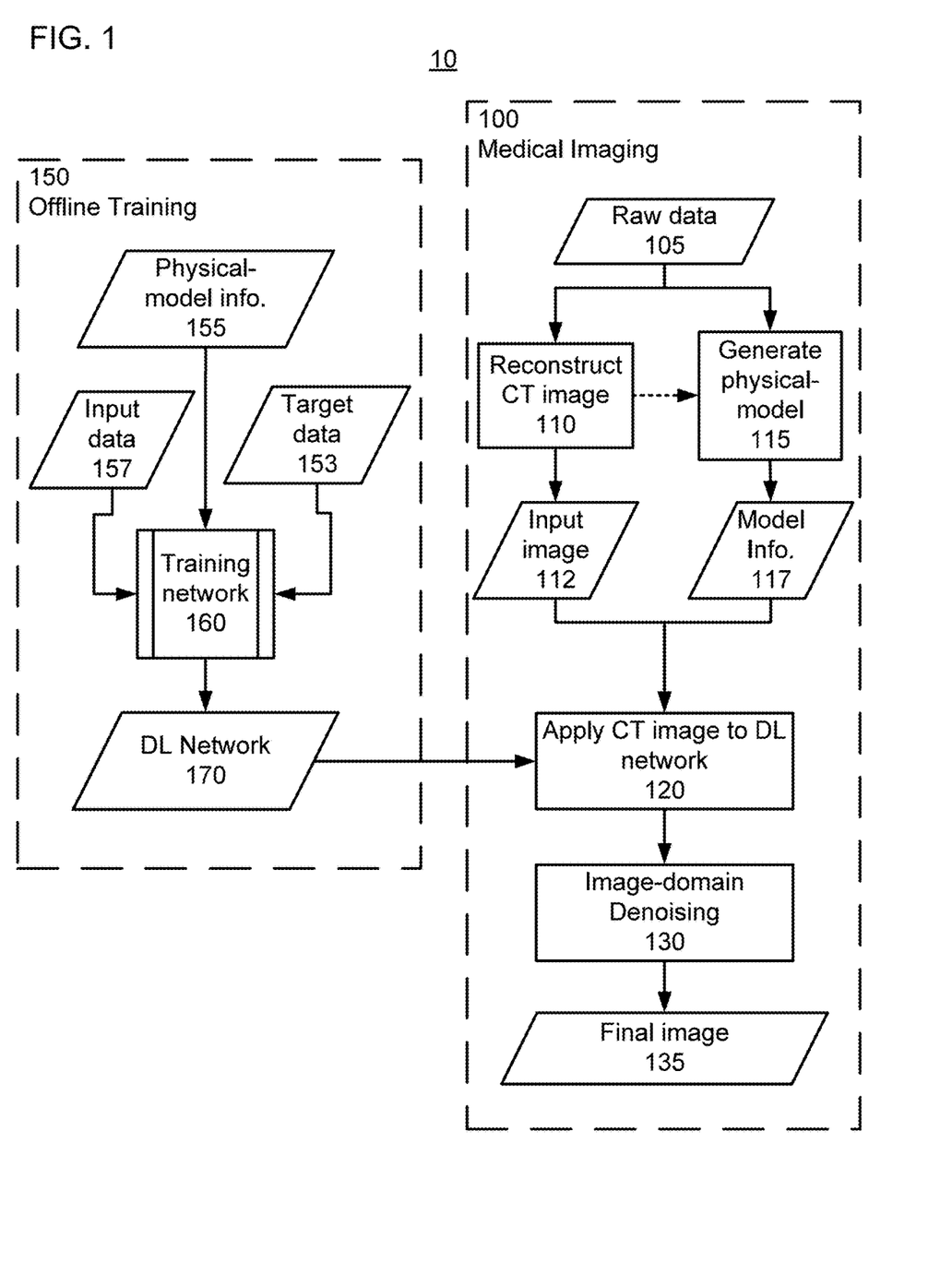
FIG. 1 shows a flow diagram of a method of training a deep learning (DL) network to use physical-model information when correcting a reconstructed image (e.g., reducing artifacts), according to one implementation.

Referring now to the drawings, wherein like reference numerals designate identical or corresponding parts throughout the several views, FIG. 1 shows a flow diagram for a non-limiting example of a method 10 for training and using a DL neural network 170 to perform image processing on a CT reconstructed image (referred to herein by the abbreviation CT image). Method 10, as illustrated in FIG. 1, uses the DL network 170 to learn how to optimally use the model information 117 to filter the CT image 112 that has been reconstructed from the raw data 105 using a fast analytical reconstruction algorithm. Method 10 includes two parts: (i) an offline training process 150 and (ii) a medical imaging process 100. That is, process 150 trains the DL network 170, and process 100 uses the trained DL network 170 to filter the CT image 112, thereby generating final CT image 135, which has improved image quality relative to the input CT image 112. In certain implementations, step 130 can be omitted.

The network 170 is trained using process 160. In process 160, a loss function is minimized by iteratively adjusting parameters of the DL network 170 (e.g., the parameters of the DL network 170 can include weighting coefficients connecting network layers, and activation functions/potentials of nodes within the layers). The optimization of the network parameters continues until stopping criteria are satisfied (e.g., a stopping criterion can be whether the value of the loss function converged to a predefined threshold) to generate the trained network 170.

The loss function compares target data 153 to an output generated from applying the input data 157 and the model information 155 as inputs to a current version of the DL network 170. For example, the input data can be CT images reconstructed using an analytical reconstruction algorithm (e.g., preferably the same analytical reconstruction algorithm that is to be used in step 110 of process 100).

The target data can be respective images generated using an IR method (or preferably an MBIR method) operating on the same raw data that is used to generate the CT images of the input data.

The CT images of the input data can be referred to as low-quality CT images, and the CT images of the target data can be referred to as high-quality CT images. For example, the low-quality CT images can have a lower image quality because they have more noise and/or artifacts than the high-quality CT images, or because they have poorer resolution than the high-quality CT images. The relative image quality can be based on an image quality metric such as (i) the peak signal-to-noise ratio, (ii) a structural similarity (SSIM) index, a visual information fidelity (VIF), a blind/referenceless image spatial quality evaluator (BRISQUE), a natural image quality evaluator (NIQE), and a perception based image quality evaluator (PIQE).

The physical-model information 155 is the same type of information as the model information 117 that is used in process 100. For an X-ray CT image reconstruction method, the physical model can include the X-ray scatter estimated from an initial model of the patient as a scattering object. Additional details of the physical-model information 155 are provided below.

In the training data, each low-quality CT image of the input data forms a pair with the corresponding high-quality CT image of the target data. The imaging scans to acquire the low-quality CT images for the input data 157 and the high-quality CT images for the target data 153 can be performed on a phantom, for example.

Applying a low-quality CT image from the input data to the current version of the DL network 170 generates an output from the network that is supposed to match as closely as possible the corresponding high-quality CT image from the target data. When the loss function indicates that the output from DL network 170 does not match the target data 153, weighting coefficients of the DL network 170 are iteratively adjusted until the output from DL network 170 does match the target data 153. That is, DL network 170 is trained by iteratively adjusting the network coefficients in the DL network 170 to minimize the difference between the filtered CT image that is output from the DL network 170 and the high-quality CT image from the target data 153. The training of the network 170 is determined to be complete when the difference is minimized between the target data and the output from the DL network 170. The question of whether or not this difference has been sufficiently minimized is resolved based on one or more predetermined stopping criteria of process 160. Once the stopping criteria have been satisfied, the trained network 170 can then be stored and then later recalled to be used in the medical imaging process 100.

In alternative implementations, the DL network 170 is implemented as a residual network (ResNet). In this case, the method described herein can filter an image by treating the difference between the low- and high-quality CT images as an additive residue that can be directly removed from the low-quality CT image. Thus, when a low-quality CT image is applied to the neural network, the network outputs an image corresponding to the difference image. Then the corrected CT image can be generated by subtracting the network output (i.e., the residue) from the low-quality CT image to generate the corrected/final CT image.

Process 100 is performed by obtaining raw data 105, e.g., by performing an X-ray CT scan to generate a sinogram (e.g., X-ray CT projections at a series of view angles).

In step 110 of process 100, a CT image is reconstructed from the denoised CT image. Preferably, a fast analytical reconstruction method—e.g., filtered back-projection (FBP)—is used to reconstruct the CT image 112. However, various methods can be used to reconstruct CT images from projection data, including filtered back-projection (FBP) and statistical iterative reconstruction (IR) algorithms.

Examples of analytical methods that can be used to reconstruct the CT image 112 include (i) a Feldkamp Davis Kress (FDK) method, (ii) a generalized FDK method, (iii) a rebinning FBP method, (iv) an n-Pi method, (v) a Pi-slant method, Katsevich's exact method, (vi) an adaptive multiple plane reconstruction (AMPR) method, (vii) an advanced single-slice rebinning (ASSR), (viii) a weigthed FBP method, and (ix) an Adaptive Iterative Dose Reduction 3D (AIDR 3D) method.

Compared to FBP reconstruction methods, IR methods can provide improved image quality. One example of an IR method is performed by conducting an optimization search to find the argument f that minimizes the objective function C(f) (also referred to as a cost function)

$$f^* = \underset{f}{\mathrm{argmin}} C(f), \text{ wherin}$$

$$C(f) = \{\tfrac{1}{2}\|f - \ell\|_W^2 + \beta U(f)\},$$

f* is the optimal image to be reconstructed, $\ell$ is the projection data representing the logarithm of the X-ray intensity of projection images taken at a series of projection angles and f is a reconstructed image of the X-ray attenuation for voxels/volume pixels (or two-dimensional pixels in a two-dimensional reconstructed image) in an image space. For the system matrix A, each matrix value $a_{ij}$ (i being a row index and j being a column index) represents an overlap between the volume corresponding to voxel $f_j$ and the X-ray trajectories corresponding to projection value $\ell_i$. The data-fidelity term $\|Af - \ell\|_W^2$ is minimized when the forward projection A of the reconstructed image f provides a good approximation to all measured projection images $\ell$. Thus, the data fidelity term is directed to solving the system matrix equation $Af = \ell$, which expresses the Radon transform (i.e., projections) of various rays from a source through an object OBJ in the space represented by f to X-ray detectors generating the values of $\ell$ (e.g., X-ray projections through the three-dimensional object OBJ onto a two-dimensional projection image $\ell$).

The notation $\|g\|_W^2$ signifies a weighted inner product of the form $g^T W g$, wherein W is the weight matrix (e.g., expressing a reliability of trustworthiness of the projection data based on a pixel-by-pixel signal-to-noise ratio). In other implementations, the weight matrix W can be replaced by an identity matrix. When the weight matrix W is used in the data fidelity term, the above IR method is referred to as a penalized weighted least squares (PLWS) approach.

The function U(p) is a regularization term, and this term is directed at imposing one or more constraints (e.g., a total variation (TV) minimization constraint), which often have the effect of smoothing or denoising the reconstructed image. The value β is a regularization parameter is a value that weights the relative contributions of the data fidelity term and the regularization term.

In step 130 of process 100, additional image-domain denoising is performed. This step is optional, and can be omitted in some implementations.

Example denoising methods include linear smoothing filters, anisotropic diffusion, non-local means, or nonlinear filters. Linear smoothing filters remove noise by convolving the original image with a convolution kernel that represents a low-pass filter or smoothing operation. For example, a Gaussian convolution kernel comprises elements determined by a Gaussian function. This convolution brings the value of each pixel into closer agreement with the values of its neighbors. Anisotropic diffusion removes noise while preserving sharp edges by evolving an image under a smoothing partial differential equation similar to the heat equation. A median filter is an example of a nonlinear filter and, if properly designed, a nonlinear filter can also preserve edges and avoid blurring. The median filter is one example of a rank-conditioned rank-selection (RCRS) filter, which can be applied to remove salt and pepper noise from an image without introducing significant blurring artifacts. Additionally, a filter using a total-variation (TV) minimization regularization term can be applied if imaged region supports an assumption of uniformity over large areas that are demarked by sharp boundaries between the uniform areas. A TV filter is another example of a nonlinear filter. Moreover, non-local means filtering is an exemplary method of determining denoised pixels using a weighted average over similar patches within the images.

Finally, a reconstructed image 135 is output having good image quality, and the reconstructed image 135 can be displayed to a user or stored for later use.

Figure 2A:
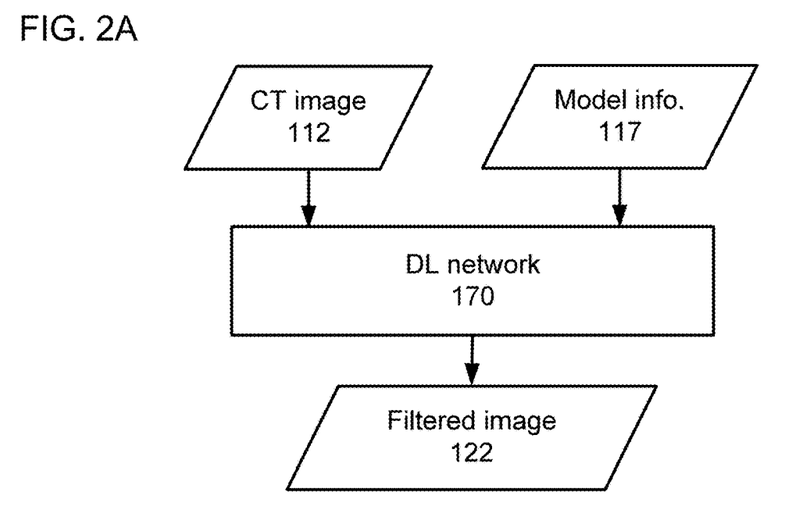
FIG. 2A shows a flow diagram for using the trained DL network to filter/correct a reconstructed image, according to one implementation.
Figure 2B:
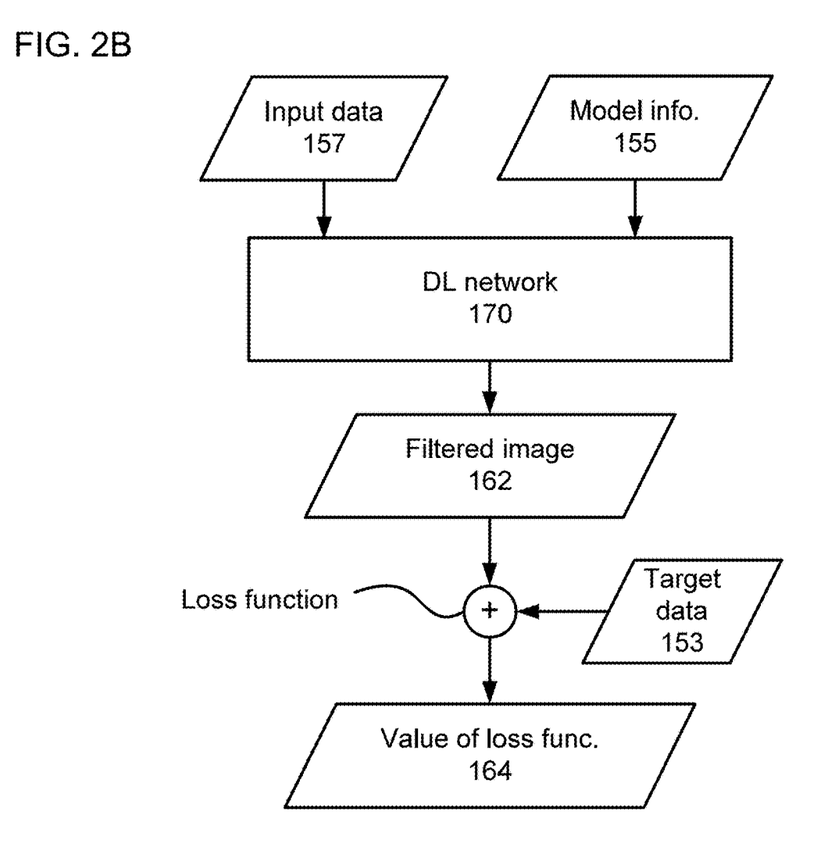
FIG. 2B shows a flow diagram for calculating a value of a loss function to train the DL network, according to one implementation.

FIGS. 2A and 2B show how the DL network 170 is used in step 120 and in process 160, respectively. In step 120, the CT image and the model information 117 are the inputs to the DL network 170, and the filtered image 122 is the output from the DL network 170. When step 130 is omitted, the filtered image 122 is the output image 135.

In process 160, the inputs to the DL network 170 are the input data 157 (i.e., a low-quality image) and the model information 155, and the output from the DL network 170 is a filtered image 162. The loss function combines the filtered image 162 and a high-quality image of the target data to generate a value representing how closely these two images agree. To train the DL network 170, the parameters of the DL network 170 are adjusted to optimize (e.g., minimize) the value of the loss function.

Regarding the model information 155 and the model information 117, many different physical models can be used to provide the information of the physical models. Also, different methods can be used to extract the information from the physical models. In general, the information of the physical models is organized/formatted the same when used in process 150 to train DL network 170, as when used in process 100. To illustrate the generation of the model information 155 and the model information 117, a non-limiting example is provided here. In this non-limiting example, the physical-model information is provided as a gradient of an objective function of an MBIR method. The MBIR method includes a physical model, and the gradient of the objective function provides information of the physical model. The DL network 170 can then be trained to use the physical-model information presented/organized in the format of a gradient of the objective function to improve the image quality based on the physical model.

As described above, IR reconstruction can be solved by minimizing an objective function C(f). In the example of the objective function C(f) illustrated above, the data fidelity term includes a system matrix A. In some model based methods, the system matrix can incorporate physical models. Further, the projection data term $\ell$ can also be modified as $P_S\ell$ to incorporate a physical model. For example, the system matrix can be modified to include a beam hardening correction, and the projection data $\ell$ can be modified to correct for scatter. That is, the objective function C(f) can be modified to be $$C(f) = \{\|A_{Tot}f - P_S\ell\|_W^2 + \beta U(f)\}$$

wherein $A_{Tot} = A_{fp} A_{bh}$ is the total system matrix, $f_p$ is the forward projection matrix, bh is the beam hardening correction, and $P_S$ is the scatter correction. Thus, the objective function C(f) can be modified to incorporate various physical models, resulting in a more accurate image reconstruction, at the expense of increasing the computational complexity of each iteration of the IR method. When the IR method is modified to incorporate a physical model, the method can be referred to as an MBIR method.

Given an objective function that incorporated one or more physical models, the information of the physical model can be generating by estimating the gradient of the objective function, i.e., $$\frac{\partial C(f)}{\partial f}.$$

In certain implementations, the gradient of the objective function (or of the data fidelity term), can be estimated using adjoint-based gradient estimation method. In certain implementations, the gradient of the objective function can be estimated using one or more iterations of an MBIR method, or using only the data-fidelity term of the MBIR method.

For example, in many IR CT methods, the final image f* can be obtained by iteratively calculating $f^{(n+1)}=f^{(n)}-\lambda \nabla C(f^{(n)})$ with sophisticated optimization algorithms, wherein $\lambda$ and $\nabla C(f^{(n)})$ are the step size and the gradient of the objective function, which is includes respective gradients of the data fidelity and regularization terms. That is, the gradient of the objective function can be estimated, e.g., by performing an iteration of an IR method, and using the step direction $f^{(n+1)}-f^{(n)}$ as the gradient direction. Thus, step 115 can be performed by performing one iteration (or more) of an MBIR method and generating the model information using the estimated gradient $\nabla C \propto f^{(1)}-f^{(0)}$. The initial guess of the reconstructed image $f^{(0)}$ can be (but does not have to be) the input image 112.

The process for generating the model information can be further generalized by noting that the objective function is not limited to the functional form provided above. More generally, model-based reconstruction can be performed by solving the optimization problem $$f^* = \underset{f}{\mathrm{argmin}}\, \mathcal{J}(G(f), P(\ell))$$

wherein $\mathcal{J}(\bullet, \bullet)$ is a data fit term (also referred to as a data-fidelity term) and $G(\bullet)$ and $P(\bullet)$ are the general physical models. Here, $\mathcal{J}(\bullet, \bullet)$ can work on both pre- and post-log measurement data and cover different metrics for different estimations including least-squares estimation, maximum likelihood estimation, and maximum a posteriori estimation. As discussed above, one method generating physical model information for inputs is to make use of gradient information, that is $$\frac{\partial \mathcal{J}}{\partial f}.$$

In the particular case that the objective function assumes the previously discussed functional form, a fully physical model reconstruction can be performed by minimizing the following regularized weighted least-squares cost function:

$$f^* = \underset{f}{\mathrm{argmin}}\, C(f) = \underset{f}{\mathrm{argmin}}\, [\|Af - P\ell\|_W^2 + \beta U(f)]$$

wherein the matrices A and P are relevant to physical models applied in image and projection domains, respectively. As discussed above, the final image f* can be obtained by iteratively calculating $f^{(n+1)}=f^{(n)}-\lambda \nabla C(f^{(n)})$. One method for generating physical model information 117 is to make use of updated image IM generated using the data-fidelity term only, that is $$IM = A^T W (A f^{(0)} - P\ell)$$

wherein $f^{(0)}$ is the CT image 112, which is calculated via analytical reconstruction.

In some implementations, the image $f^{(0)}$ can be different from the CT image 112 (e.g., $f^{(0)}$ can be reconstructed using different reconstruction kernel than is used to reconstruct CT image 112). In certain implementations, the first iteration of the data fidelity term IM is used as the model information 117.

In other implementations, the model information 117 can be the estimate of the gradient (e.g., $IM-f^{(0)}$, $f^{(1)}-f^{(0)}$, $f^{(n)}-f^{(0)}$, $f^{(n)}-f^{(n-1)}$, etc.). In general, the same method as used for generating the model information 115 is also used for generating the model information 155.

Whereas the model information 155 can be generated using only one (or a few) iterations of the MBIR method, to generate the target data the MBIR method can be performed to convergence. Also, whereas the model information 155 can be generated using the data fidelity term alone, the MBIR method can be performed using both the data fidelity term and the regularization term to generate the target data.

As discussed above, various physical models can be incorporated into the objective function, and these physical models are not limited to the scatter correction $P_S$, and beam hardening correction bh mentioned above. Multiple factors can affect the CT image quality, such as the CT system (e.g., the gantry, X-ray source, detectors, etc.) and also physical mechanism (e.g., scattering in patient and the polychromatic aspects of the radiation). Accordingly, model-based reconstruction can improve imaging performance by considering both of advanced physical models as well as the integration of the various physical mechanism. These disparate physical models can be integrated into the data fidelity term of the objective function in both the image domain (e.g., the physical model can be incorporated into the system matrix A) and the projection domain (e.g., the physical model can be incorporated into the matrix P). More generally, operations in the image domain can be represented by the function G(f), and operations in the projection domain can be represented by the function $P(\ell)$.

In certain implementations, the physical models can include a deterministic radiative transfer scatter model for total scatter correction ($P_S$), as discussed in U.S. patent application Ser. No. 15/210,657, U.S. patent application Ser. No. 15/436,043, U.S. patent application Ser. No. 16/392,177, and U.S. patent application Ser. No. 16/252,392, which are incorporated herein by reference in its entirety. For example, the initial reconstructed image $f^{(0)}$ can be used to estimate the scatter contribution to each of the pixel values in the projection data $\ell$, and the scatter correction can remove the contribution due to scatter such that the value $P_S \ell$ is the primary signal, which is the total signal minus the scatter signal.

In certain implementations, the physical models can include a multiple material beam hardening model for beam hardening correction ($A_{bh}$), as discussed in I. Hein, Z. Yu, S. Nakanishi, "Three-dimensional two material based beam hardening correction for iterative reconstruction", *Proc. 4th Int. Conf. Image Formation X-Ray Comput. Tomogr.*, pp. 455-458, 2016, which is incorporated herein by reference in its entirety. For example, the initial reconstructed image $f^{(0)}$, can be segmented into material components (e.g., using a material decomposition or by mapping the Hounsfield Units in the respective voxels to respective material components, e.g., bone, water, and a combination of bone and water) and then forward projecting using the material dependent spectral attenuation to account for the beam hardening corrections. Additionally, when the projection data $\ell$ is generated using dual-energy or spectral CT, material decomposition can be used to separate the attenuation in the respective voxels into material components, which are then used for the forward projection to account for beam-hardening corrections.

In certain implementations, the physical models can include a simulated and/or experimental system response simulation algorithm for source and detector blurring ($A_{psf}$), as discussed in U.S. patent application Ser. No. 14/681,797, which is incorporated herein by reference in its entirety. Further, the physical models can include a simulated and/or experimental system response for detector nonlinearities as discussed in U.S. patent application Ser. No. 14/593,818, which is incorporated herein by reference in its entirety. That is, the detector correction $A_{psf}$ can account for a point spread function arising from the spatial resolution limitations of the detector elements (e.g., diffraction optical photons, and charge sharing in direct detectors), and, in certain implementations, the detector correction $A_{psf}$ can account for detector non-linearities due to k-escape, energy-resolution limitations, pill up, and for gamma-ray detectors Compton scattering.

In certain implementations, the physical models can include an advanced footprint method for precise forward projection ($A_{fp}$) to account for the system geometry, as discussed in D. De Man and s. Basu, "Distance-driven projection and backprojection in three dimensions," Phys. Med. Biol., vol. 49, issue 11, page 2463 (2004), which is incorporated herein by reference in its entirety. For example, the precise forward projection model ($A_{fp}$) can us distance-driven projection and backprojection that provides a highly sequential memory access pattern. The forward projection model ($A_{fp}$) can be performed by mapping pixel boundaries and detector boundaries to a common axis, and then applying a kernel operation to map data from one set of boundaries to another.

Distance-driven projection can be better understood in the context of pixel-driven backprojection and ay-driven projection. Pixel-driven backprojection works by connecting a line from the focal spot through the center of the pixel of interest to the detector. Once a location of intersection on the detector is calculated, a value is obtained from the detector by (typically linear) interpolation, and the result is accumulated in the pixel. Ray-driven projection works by connecting a line from the focal spot through the image to the center of the detector cell of interest. For every image row (or column), a location of intersection is calculated, a value is obtained from the image row, typically by linear interpolation, and the result is accumulated in the detector cell.

Distance-driven projection/back-projection combines the advantages of the ray-driven and pixel-driven methods. First, every view (or source position) defines a bijection between the position on the detector and the position within an image row (or column) (i.e., every point within an image row is mapped uniquely onto a point on the detector, and vice versa). This allows a length of overlap to be defined between each image pixel and each detector cell. To calculate this length of overlap we could map all pixel boundaries in an image row of interest onto the detector, or all detector cell boundaries onto the centerline of the image row of interest. In practice, both sets of boundaries are mapped onto a common line, which is achieved by connecting all pixel boundaries and all detector cell boundaries with the source and calculating the x-intercepts. Based on these boundaries, the length of overlap is calculated between each image pixel and each detector cell, and length of overlap is used to normalize the weight used in projection and backprojection. This corresponds to applying the distance-driven kernel operation to the mapped boundary locations, which is achieved by performing a loop over all boundaries (e.g., starting at the boundary with the smallest x intercept and stopping at the boundary with the highest x intercept). The normalization consists of dividing by the pixel width (for FBP) or by the detector width (for simulation).

The total system matrix is obtained by combining the respective corrections, e.g., $A_{Tot}=A_{geo}A_{psf}A_{fp}A_{bh}$. Finally, the operators (A and P) in the data-fidelity term of the objective function $$C(f)=\|Af-P\ell\|_W^2+\beta U(f)$$

for the iterative reconstruction become $A_{geo}A_{psf}A_{fp}A_{bh}$ and $P_s$, when combing the simple system geometry model $A_{geo}$.

Now a more detailed description of training a DL network is provided (e.g., process 160). Here, the target data 153 are high-quality CT images reconstructed using an IR method, and the input data 157 are low-quality CT images reconstructed using a fast analytical method, as described above.

Figure 3:
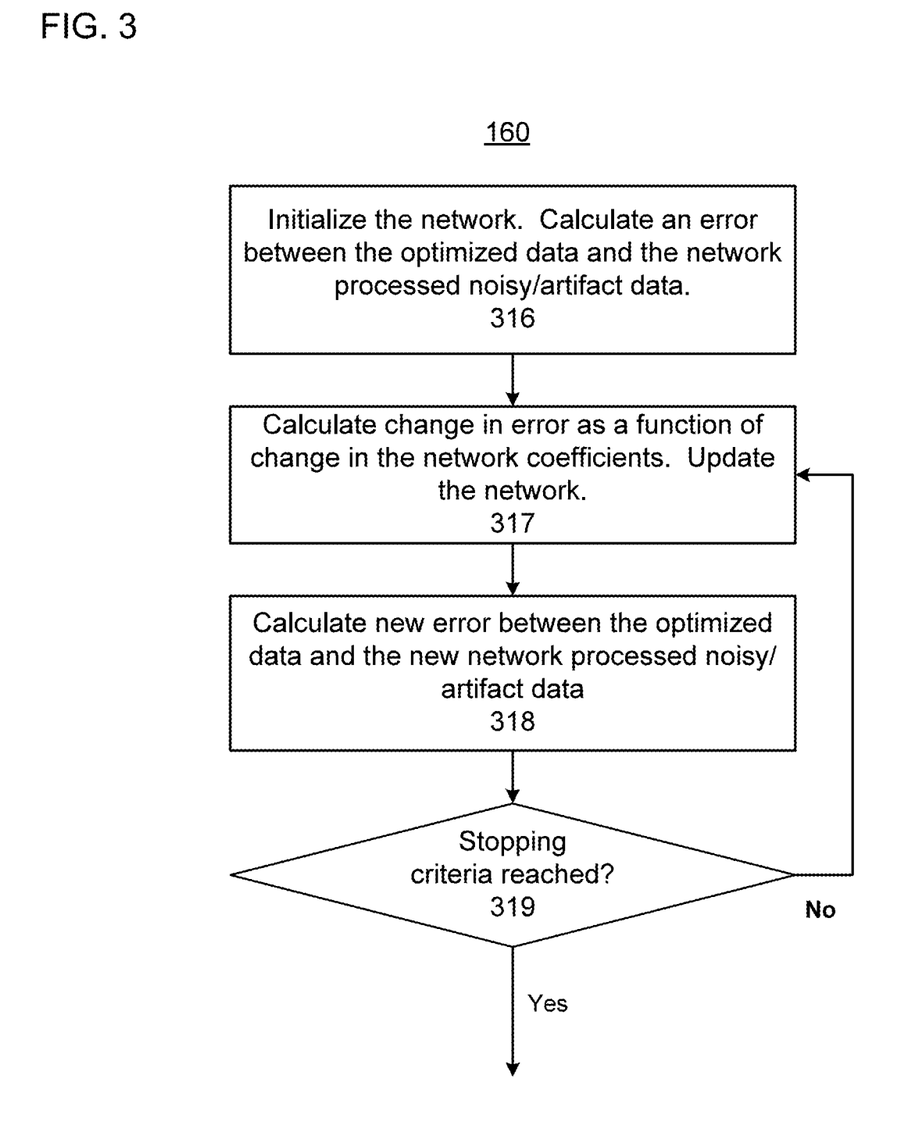
FIG. 3 shows a flow diagram of the process to train the DL network by iteratively adjusting coefficients of the DL network to optimize a loss-error function, according to one implementation.

FIG. 3 shows a flow diagram of one implementation of the training process 160. In process 160, input data 157 and target data 153 are used as training data to train a DL network 170, resulting in the DL network 170 being output from step 319 of process 160. The offline DL training process 160 trains the DL network 170 using a large number of reconstructed CT images of the input data 157 that are paired with corresponding physical-model information 155 and reconstructed CT images of the target data 153 to train the DL network 170 to produce, from the input CT images 157, filtered CT images resembling the target CT images 153.

In process 160, a set of training data is obtained, and the network 170 is iteratively updated to reduce the error (e.g., the value produced by a loss function). The DL network infers the mapping implied by the training data, and the loss function produces an error value related to the mismatch between CT images of the target data 153 and the result produced by applying a current incarnation of the DL network 170 to the CT images of the input data 157. For example, in certain implementations, the loss function can use the mean-squared error to minimize the average squared error. In the case of a of multilayer perceptrons (MLP) neural network, the backpropagation algorithm can be used for training the network by minimizing the mean-squared-error-based loss function using a (stochastic) gradient descent method.

In step 316 of process 160, an initial guess is generated for the coefficients of the DL network 170. For example, the initial guess can be based on a priori knowledge of the region being imaged or one or more exemplary denoising methods, edge-detection methods, and/or blob detection methods. Additionally, the initial guess can be based on one of a LeCun initialization, an Xavier initialization, and a Kaiming initialization.

Steps 316 through 319 of process 160 provide a non-limiting example of an optimization method for training the DL network 170.

An error is calculated (e.g., using a loss function or a loss function) to represent a measure of the difference (e.g., a distance measure) between the CT images of the target data 153 (i.e., ground truth) and the CT images of the input data 157 after applying a current version of the network 170. The error can be calculated using any known loss function or distance measure between the image data, including those loss functions described above. Further, in certain implementations the error/loss function can be calculated using one or more of a hinge loss and a cross-entropy loss. In certain implementations, the loss function can be the $\ell_p$-norm of the difference between the target data and the result of applying the input data to the DL network 170. Different values of "p" in the $\ell_p$-norm can be used to emphasize different aspects of the noise. Further, a weighting mask (e.g., based on the attenuation coefficient of signal intensity) can be applied on a pixel-by-pixel basis to the difference between the target data and the result generated from the input data. In certain implementations, rather than minimizing an $\ell_p$-norm of the difference between the target data and the result from the input data, the loss function can represent a similarity (e.g., using a peak signal-to-noise ratio (PSNR) or a structural similarity (SSIM) index).

In certain implementations, the training is performed by minimizing the following loss function $$\hat{\theta} = \operatorname*{argmin}_{\theta} \frac{1}{N} \sum_n L(\bar{y}^{(n)}, f(y^{(n)} \mid \theta, h)) + \beta R(h)$$

where θ are the adjustable weighting coefficients of the DL network 170, h are the non-adjustable parameters (e.g., parameters selected by a user, such as the choice of reconstruction kernel), $y^{(n)}$ represents the nth input CT image, $\bar{y}^{(n)}$ represents the nth target CT image. The number N is the total number of training projections. In certain implementations, the following weighted mean absolute error loss function is used $$L(\bar{y}, y) = \sum_j d_j |y_j - \bar{y}_j|$$

wherein $d_j$ is the weight which has the form $$d_j = \bar{y}_j^p$$

with p being a scalar. The choice of this weight is inspired by the statistical mean estimation method where $d_j$ is often necessarily chosen to be the inverse of data noise variance. To handle the overfitting issue an additional regularization R on h is used, which is given by R (h)=$\Sigma_j h_j$. The regularization strength can be tuned thru the parameter β.

In certain implementations, the network 170 is trained using backpropagation. Backpropagation can be used for training neural networks and is used in conjunction with gradient descent optimization methods. During a forward pass, the algorithm computes the network's predictions based on the current parameters θ. These predictions are then input into the loss function, by which they are compared to the corresponding ground truth labels (i.e., the high-quality target data 153). During the backward pass, the model computes the gradient of the loss function with respect to the current parameters, after which the parameters are updated by taking a step of size of a predefined size in the direction of minimized loss (e.g., in accelerated methods, such that the Nesterov momentum method and various adaptive methods, the step size can be selected to more quickly converge to optimize the loss function).

The optimization method by which the backprojection is performed can use one or more of gradient descent, batch gradient descent, stochastic gradient descent, and mini-batch stochastic gradient descent. The forward and backwards passes can be performed incrementally through the respective layers of the network. In the forward pass, the execution starts by feeding the inputs through the first layer, thus creating the output activations for the subsequent layer. This process is repeated until the loss function at the last layer is reached. During the backward pass, the last layer computes the gradients with respect to its own learnable parameters (if any) and also with respect to its own input, which serves as the upstream derivatives for the previous layer. This process is repeated until the input layer is reached.

Returning to FIG. 3, step 317 of process 160 determines a change in the error as a function of the change in the network can be calculated (e.g., an error gradient), and this change in the error can be used to select a direction and step size for a subsequent change to the weights/coefficients of the DL network 170. Calculating the gradient of the error in this manner is consistent with certain implementations of a gradient descent optimization method. In certain other implementations, this step can be omitted and/or substituted with another step in accordance with another optimization algorithm (e.g., a non-gradient descent optimization algorithm like simulated annealing or a genetic algorithm), as would be understood by one of ordinary skill in the art.

In step 317 of process 160, a new set of coefficients are determined for the DL network 170. For example, the weights/coefficients can be updated using the changed calculated in step 317, as in a gradient descent optimization method or an over-relaxation acceleration method.

In step 318 of process 160, a new error value is calculated using the updated weights/coefficients of the DL network 170.

In step 319, predefined stopping criteria are used to determine whether the training of the network is complete. For example, the predefined stopping criteria can evaluate whether the new error and/or the total number of iterations performed exceed predefined values. For example, the stopping criteria can be satisfied if either the new error falls below a predefined threshold or if a maximum number of iterations is reached. When the stopping criteria is not satisfied the training process performed in process 160 will continue back to the start of the iterative loop by returning and repeating step 317 using the new weights and coefficients (the iterative loop includes steps 317, 318, and 319). When the stopping criteria are satisfied the training process performed in process 160 is completed.

Figure 4:
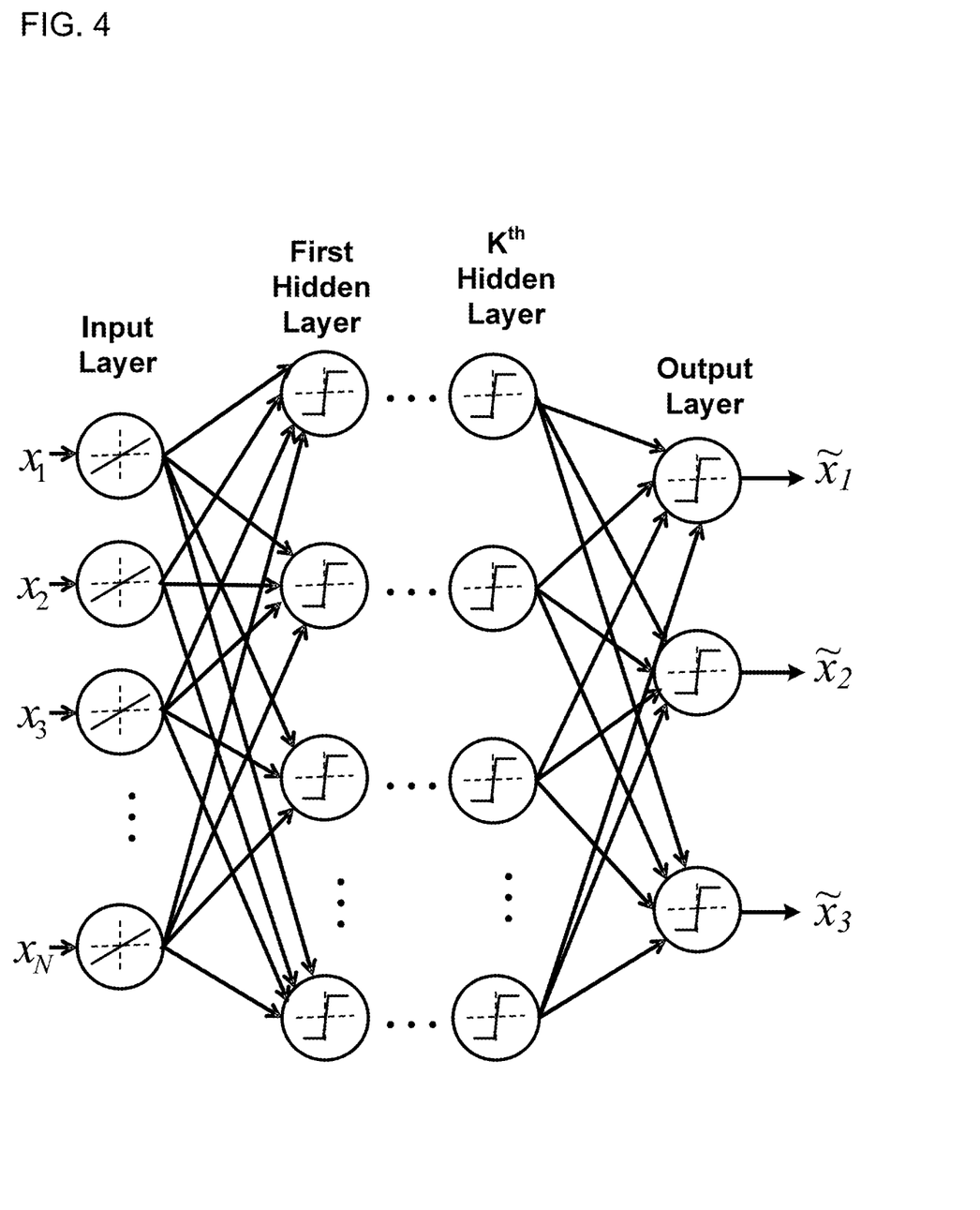
FIG. 4 shows an example of a DL network, according to one implementation.
Figure 5:
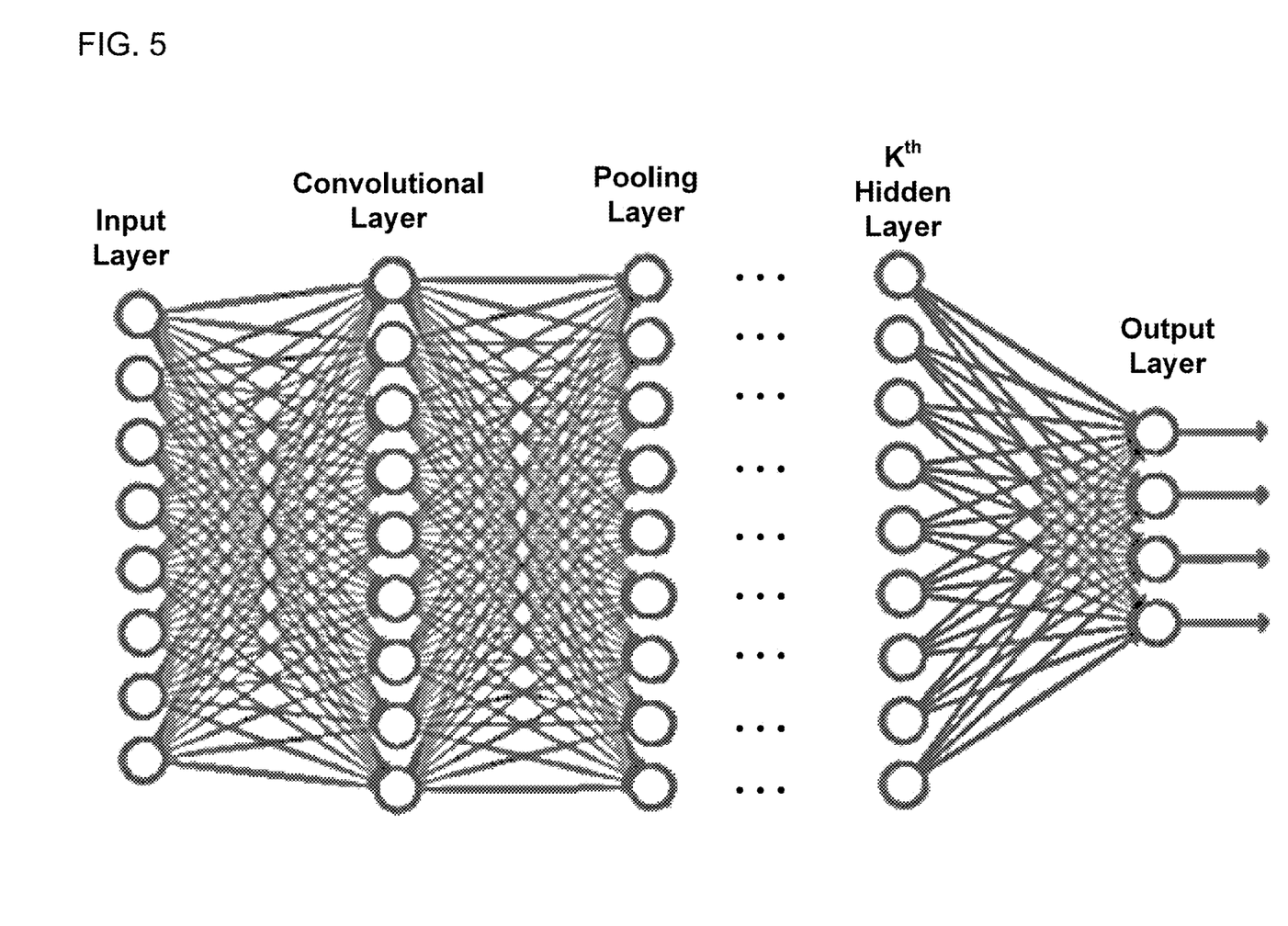
FIG. 5 shows an example of a type of DL network referred to as a convolutional neural network (CNN), according to one implementation.

FIGS. 4 and 5 show two examples of the inter-connections between layers in the DL network 170. The DL network 170 can include fully connected, convolutional, and the pooling layer, all of which are explained below. In certain preferred implementations of the DL network 170, convolutional layers are placed close to the input layer, whereas fully connected layers, which perform the high-level reasoning, are place further down the architecture towards the loss function. Pooling layers can be inserted after convolutions and proved a reduction lowering the spatial extent of the filters, and thus the amount of learnable parameters. Activation functions are also incorporated into various layers to introduce nonlinearity and enable the network to learn complex predictive relationships. The activation function can be a saturating activation functions (e.g., a sigmoid or hyperbolic tangent activation function) or rectified activation function (e.g., the Rectified Linear Unit (ReLU) applied in the first and second examples discussed above). The layers of the DL network 170 can also incorporate batch normalization, as also exemplified in the first and second examples discussed above.

FIG. 4 shows an example of a general artificial neural network (ANN) having N inputs, K hidden layers, and three outputs. Each layer is made up of nodes (also called neurons), and each node performs a weighted sum of the inputs and compares the result of the weighted sum to a threshold to generate an output. ANNs make up a class of functions for which the members of the class are obtained by varying thresholds, connection weights, or specifics of the architecture such as the number of nodes and/or their connectivity. The nodes in an ANN can be referred to as neurons (or as neuronal nodes), and the neurons can have inter-connections between the different layers of the ANN system. The synapses (i.e., the connections between neurons) store values called "weights" (also interchangeably referred to as "coefficients" or "weighting coefficients") that manipulate the data in the calculations. The outputs of the ANN depend on three types of parameters: (i) the interconnection pattern between the different layers of neurons, (ii) the learning process for updating the weights of the interconnections, and (iii) the activation function that converts a neuron's weighted input to its output activation.

Mathematically, a neuron's network function m(x) is defined as a composition of other functions $n_i(x)$, which can further be defined as a composition of other functions. This can be conveniently represented as a network structure, with arrows depicting the dependencies between variables, as shown in FIG. 4. For example, the ANN can use a nonlinear weighted sum, wherein m(x)=K ($\Sigma_i w_i n_i(x)$), where K (commonly referred to as the activation function) is some predefined function, such as the hyperbolic tangent.

In FIG. 4 (and similarly in FIG. 5), the neurons (i.e., nodes) are depicted by circles around a threshold function. For the non-limiting example shown in FIG. 4, the inputs are depicted as circles around a linear function, and the arrows indicate directed connections between neurons. In certain implementations, the DL network 170 is a feedforward network.

FIG. 5 shows a non-limiting example in which the DL network 170 is a convolutional neural network (CNN). CNNs are type of ANN that has beneficial properties for image processing, and, therefore, have specially relevancy for the applications of image denoising. CNNs use feedforward ANNs in which the connectivity pattern between neurons can represent convolutions in image processing. For example, CNNs can be used for image-processing optimization by using multiple layers of small neuron collections which process portions of the input image, called receptive fields. The outputs of these collections can then tiled so that they overlap, to obtain a better representation of the original image. This processing pattern can be repeated over multiple layers having alternating convolution and pooling layers.

Following after a convolutional layer, a CNN can include local and/or global pooling layers, which combine the outputs of neuron clusters in the convolution layers. Additionally, in certain implementations, the CNN can also include various combinations of convolutional and fully connected layers, with pointwise nonlinearity applied at the end of or after each layer.

Figure 6:
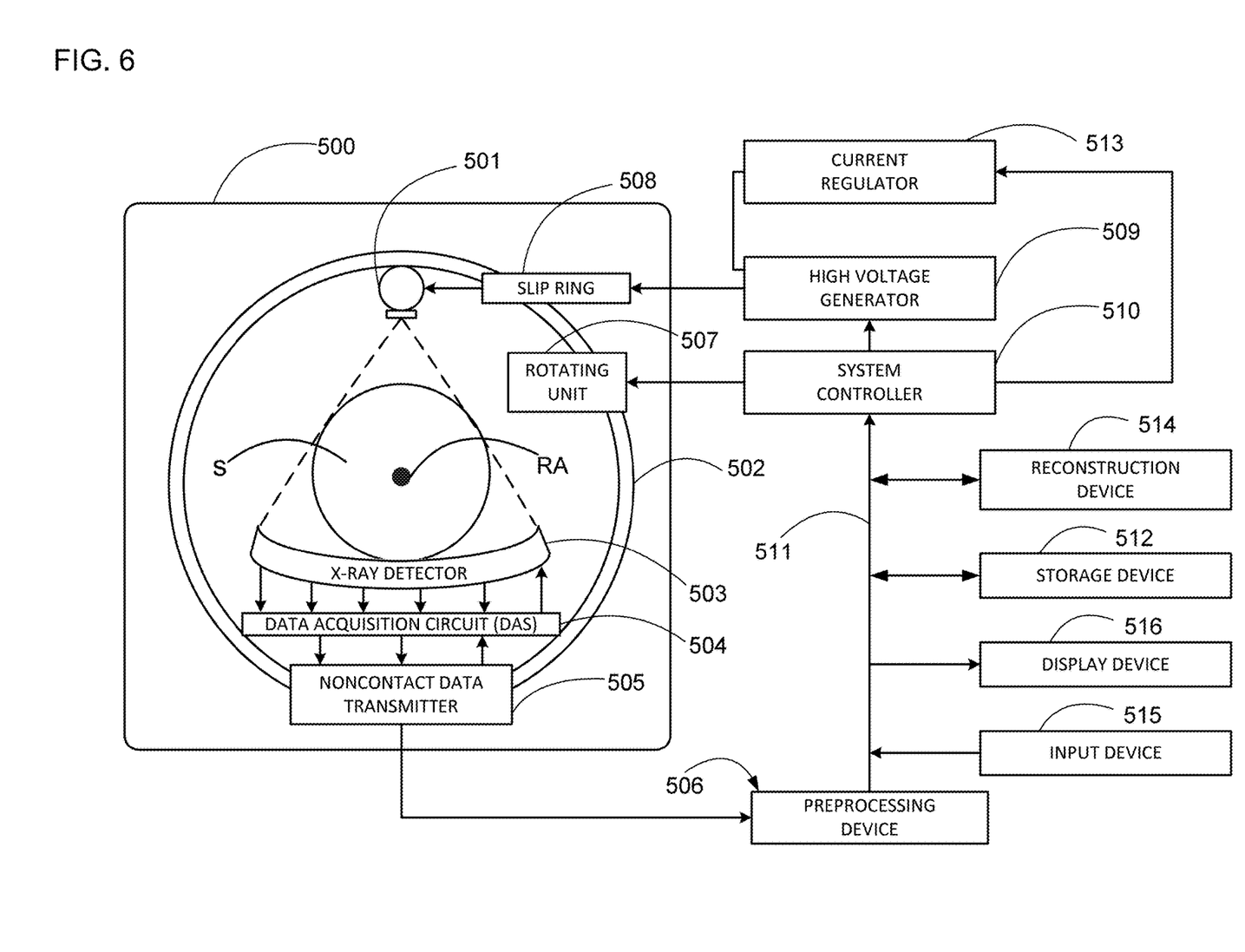
FIG. 6 shows a schematic diagram of an X-ray computed tomography (CT) scanner, according to one implementation.

FIG. 6 illustrates a non-limiting example of a CT scanner. As shown in FIG. 6, a radiography gantry 500 is illustrated from a side view and further includes an X-ray tube 501, an annular frame 502, and a multi-row or two-dimensional-array-type X-ray detector 503. The X-ray tube 501 and X-ray detector 503 are diametrically mounted across an object OBJ on the annular frame 502, which is rotatably supported around a rotation axis RA.

The multi-slice X-ray CT apparatus further includes a high voltage generator 509 that generates a tube voltage applied to the X-ray tube 501 through a slip ring 508 so that the X-ray tube 501 generates X-rays. The X-rays are emitted towards the object OBJ, whose cross sectional area is represented by a circle. For example, the X-ray tube 501 having an average X-ray energy during a first scan that is less than an average X-ray energy during a second scan. Thus, two or more scans can be obtained corresponding to different X-ray energies. The X-ray detector 503 is located at an opposite side from the X-ray tube 501 across the object OBJ for detecting the emitted X-rays that have transmitted through the object OBJ. The X-ray detector 503 further includes individual detector elements or units.

The CT apparatus further includes other devices for processing the detected signals from X-ray detector 503. A data acquisition circuit or a Data Acquisition System (DAS) 504 converts a signal output from the X-ray detector 503 for each channel into a voltage signal, amplifies the signal, and further converts the signal into a digital signal.

The above-described data is sent to a preprocessing circuitry 506, which is housed in a console outside the radiography gantry 500 through a non-contact data transmitter 505. The preprocessing circuitry 506 performs certain corrections, such as sensitivity correction on the raw data. A storage 512 stores the resultant data, which is also called projection data at a stage immediately before reconstruction processing. The storage 512 is connected to a processing circuitry 510 through a data/control bus 511, together with a reconstruction device 514, input interface 515, and display 516. The processing circuitry 510 controls a current regulator 513 that limits the current to a level sufficient for driving the CT system.

The storage 512 can store the measurement value representative of the irradiance of the X-rays at the X-ray detector unit 503. Further, the storage 512 can store a dedicated program for executing method 10.

The reconstruction circuitry 514 can execute various steps of method 10. Further, reconstruction circuitry 514 can execute pre-reconstruction processing image processing such as volume rendering processing and image difference processing as needed.

The pre-reconstruction processing of the projection data performed by the preprocessing circuitry 506 can include correcting for detector calibrations, detector nonlinearities, and polar effects, for example.

Post-reconstruction processing performed by the reconstruction circuitry 514 can include filtering and smoothing the image, volume rendering processing, and image difference processing as needed. The image reconstruction process can implement various steps of method 10. The reconstruction circuitry 514 can use the memory to store, e.g., projection data, reconstructed images, calibration data and parameters, and computer programs.

The various circuitries (e.g., the reconstruction circuitry 514 and preprocessing circuitry 506) can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the storage 512 can be non-volatile, such as ROM, EPROM, EEPROM or FLASH memory. The storage 512 can also be volatile, such as static or dynamic RAM, and a processor, such as a microcontroller or microprocessor, can be provided to manage the electronic memory as well as the interaction between the FPGA or CPLD and the memory.

In one implementation, the reconstructed images can be displayed on a display 516. The display 516 can be an LCD display, CRT display, plasma display, OLED, LED or any other display known in the art.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An apparatus, comprising:
    circuitry configured to
        obtain projection data representing X-rays detected by a plurality of detectors,
        reconstruct a first image from the projection data using a first computed tomography (CT) method,
        generate data of a physical model based on the projection data and/or the first image,
        acquire a neural network, the neural network having been trained using a training dataset and physical-model information, the training dataset including input data and target data, the input data being images that are reconstructed using the first CT method, the target data being images that are reconstructed using a second CT method, and the physical-model information being generated in a same manner as the generation of the data of the physical model, and
        apply the first image and the data of a physical model as inputs to the neural network to thereby generate a second image as an output from the neural network, the second image having an improved image-quality relative to the first input image.

2. The apparatus according to claim 1, wherein the circuitry is further configured to
    generate the data of the physical model by performing an iteration or a portion of an iteration of a model-based iterative reconstruction (MBIR) method for CT, and
    reconstruct the first image using the first computed tomography (CT) method, which is an analytical reconstruction method.

3. The apparatus according to claim 1, wherein the circuitry is further configured to generate the data of the physical model by calculating a data-fidelity term of an objective function for a model-based iterative reconstruction (MBIR) method to generate an updated image as the data of the physical model.

4. The apparatus according to claim 1, wherein the circuitry is further configured to generate the data of the physical model, and the physical model includes at least one of a scatter model, a beam-hardening model, a detector model, a forward projection model, or a system geometry model.

5. The apparatus according to claim 1, wherein the circuitry is further configured to generate the data of the physical model using an estimate of a gradient of an objective function of a model-based iterative reconstruction (MBIR) method.

6. The apparatus according to claim 1, wherein the circuitry is further configured to acquire the neural network, and the neural network has been trained using the target data comprising images that are reconstructed using the second CT method, which is an iterative reconstruction (IR) method, and using input data comprising images that are reconstructed using the first CT method, which is an analytical reconstruction method.

7. The apparatus according to claim 6, wherein the circuitry is further configured to acquire the neural network, wherein the neural network has been trained using the target data that is reconstructed using the second CT method, and the second CT method is a model-based iterative reconstruction (MBIR) method that incorporates the physical model.

8. The apparatus according to claim 1, wherein the circuitry is further configured to acquire the neural network, wherein the neural network is a residual network, and the second image is generated by subtracting an output of the network from the first image.

9. The apparatus according to claim 1, wherein the circuitry is further configured to train the neural network by
    obtaining the training dataset comprising the input data and the target data, the second CT method used to reconstruct the images of the target data being an iterative reconstruction (IR) method,
    using the neural network to generate filtered images from the respective images of the input data by applying a given image of the input data together with the physical-model information corresponding to the given image to the neural network, thereby generating a corresponding filtered image, and
    training the neural network by iteratively adjusting weighting coefficients of the neural network to minimize a value of a loss function, the loss function measuring a disagreement between the neural network and an image of the target data that corresponds to the given image of the input data.

10. The apparatus according to claim 9, wherein the circuitry is further configured to train the neural network wherein the loss function includes a peak signal to noise ratio, a structural similarity index, or an $\ell_p$-norm of a difference between the respective images of the target data and the filtered images corresponding to the images of the target input data.

11. The apparatus according to claim 1, wherein the circuitry is further configured to generate the data of the physical model, and the physical model includes one or more models selected from (i) an X-ray scatter model based on the first CT image, (ii) a beam hardening model, (iii) a spatial-resolution detector model, (iv) a detector response model, (v) a system geometry model, and (vi) a forward projection model.

12. The apparatus according to claim 1, further comprising
    an X-ray source configured to emit X-rays as the radiation, and
    a detector array including the plurality of detectors, the detector array being arranged across an opening in a gantry diametrically opposite to the X-ray source, and the detector array being configured to receive the X-rays emitted from the X-ray source and generate the projection data.

13. A method, comprising:
    obtaining projection data representing X-rays detected by a plurality of detectors;
    reconstructing a first image from the projection data using a first computed tomography (CT) method;
    generating data of a physical model using the projection data and/or the first image;

acquiring a neural network, the neural network having been trained using a training dataset and physical-model information, the training dataset including input data and target data, the input data being images that are reconstructed using the first CT method, the target data being images that are reconstructed using a second CT method, and the physical-model information being generated in a same manner as the generation of the data of the physical model; and applying the first image and the data of a physical model as inputs to the neural network to thereby generate a second image as an output from the neural network, the second image having an improved image-quality relative to the first input image.

14. The method according to claim 13, wherein the step of generating the data of the physical model is performed using an estimate of a gradient of an objective function of a model-based iterative reconstruction (MBIR) method.

15. The method according to claim 13, wherein the step of generating the data of the physical model includes that the physical model includes at least one of a scatter model, a beam-hardening model, a detector model, a forward projection model, or a system geometry model.

16. The method according to claim 13, wherein the step of acquiring the neural network further includes that the neural network has been trained using the target data comprising images that are reconstructed using the second CT method, which is an iterative reconstruction (IR) method, and using input data comprising images that are reconstructed using the first CT method, which is an analytical reconstruction method.

17. The method according to claim 13, wherein
the step of generating the data of the physical model further includes that the physical model includes one or more models selected from (i) an X-ray scatter model based on the first CT image, (ii) a beam hardening model, (iii) a spatial-resolution detector model, (iv) a detector response model, (v) a system geometry model, and (vi) a forward projection model.

18. The method according to claim 13, further comprising training the neural network by
obtaining the training dataset comprising the input data and the target data, the second CT method used to reconstruct the images of the target data being an iterative reconstruction (IR) method, using the neural network to generate filtered images from the respective images of the input data by applying a given image of the input data together with the physical-model information corresponding to the given image to the neural network, thereby generating a corresponding filtered image, and training the neural network by iteratively adjusting weighting coefficients of the neural network to minimize a value of a loss function, the loss function measuring a disagreement between the neural network and an image of the target data that corresponds to the given image of the input data.

19. The method according to claim 18, wherein the step of training the neural network further includes that the loss function includes a peak signal to noise ratio, a structural similarity index, or an $\ell_p$-norm of a difference between the respective images of the target data and the filtered images corresponding to the images of the target input data.

20. A non-transitory computer-readable storage medium including executable instructions, which when executed by circuitry, cause the circuitry to perform the method according to claim 13.

* * * * *